(12) United States Patent
Hill et al.

(10) Patent No.: US 6,991,915 B2
(45) Date of Patent: Jan. 31, 2006

(54) MODIFIED CDC14 PHOSPHATASE PROTEINS AND CONSTRUCTS FOR IMPROVED EXPRESSION AND PURIFICATION

(75) Inventors: Craig Hill, Burlingame, CA (US); Joseph Buggy, San Carlos, CA (US)

(73) Assignee: Applera Corporation, Norwalk, CT (US)

( * ) Notice: Subject to any disclaimer, the term of this patent is extended or adjusted under 35 U.S.C. 154(b) by 493 days.

(21) Appl. No.: 10/202,879

(22) Filed: Jul. 26, 2002

(65) Prior Publication Data

US 2004/0018604 A1    Jan. 29, 2004

(51) Int. Cl.
  *C12Q 1/42*   (2006.01)
  *C12N 9/16*   (2006.01)

(52) U.S. Cl. .......................... 435/21; 435/196
(58) Field of Classification Search ............... 435/196, 435/195, 21; 536/23.1, 23.2
  See application file for complete search history.

(56) References Cited

U.S. PATENT DOCUMENTS 6,331,614 B1   12/2001   Wong et al. ............ 536/23.5

OTHER PUBLICATIONS

Liwu Li et al.; "A Family of Putative Tumor Suppresors Is Structurally and Funtionally Conserved in Humans and Yeast;" The Journal of Biological Chemistry; vol. 272 No. 47, pp. 29403-29406; Nov. 21, 1997.

Liwu Li et al.; "The Human Cdc14 Phosphatases Interact with and Dephosphorylate the Tumor Suppressor Protein p53;" The Journal of Biological Chemistry vol. 275 No. 4 pp. 2410-2414; Jan. 28, 2000.

Alexander Wong et al. "Genomic Structure, Chromosonal Location, and Mutation Analysis of the Human CDC14A Gene;" Genomics vol. 59 pp. 248-251; Apr. 2, 1999.

Novagen; Product Catalog Dec. 1998 for their pET-30a-c(+) Vectors.

Genbank entry, GI: 15451928.
Genbank entry, GI: 15451929.

*Primary Examiner*—Nashaat T. Nashed

(74) *Attorney, Agent, or Firm*—Celera Genomics; Justin D. Karjala

(57) ABSTRACT

The present invention provides modified Cdc14 phosphatase proteins, and novel constructs for expression thereof, in which the sequence C-terminal to the catalytic domain has been deleted. This modification results in the expression of a single form of the enzyme, enabling purification of a homogeneous preparation of active enzyme at a high yield.

3 Claims, 2 Drawing Sheets

Cdc14AS amino acid sequence (SEQ ID NO:1):

MHHHHHSSGLVPRGSGMKETAAAKFERQHMDSPDLGTDDDDKAMADIGSEFAAESGELIGACEFMKDRLYFATLRNRP
KSTVNTHYFSIDEELVYENFYADFGPLNLAMVYRYCCKLNKKLKSYSLSRKKIVHYTCFDQRKRANAAFLIGAYAVIYL
KKTPEEAYRALLSGSNPPYLPFRDASFGNCTYNLTILDCLQGIRKGLQHGFFDFETFDVDEYEHYERVENGDFNWIVPG
KFLAFSGPHPKSKIENGYPLHAPEAYFPYFKKHNVTAVVRLNKKIYEAKRFTDAGFEHYDLFFIDGSTPSDNIVRRFLN
ICENTEGAIAVHCKAGLGRTGTLIACYVMKHYRFTHAEIIAWIRICRPGSIIGPQQHFLEEKQASLWVQGDIFRSKLKN
RPSSEGSINKILSGLDDMSIGGNLSKTQNMERFG

Amino acid residues 2-378 of the Cdc14A1 phosphatase protein (SEQ ID NO:2), and
the encoding nucleic acid sequence (SEQ ID NO:3):

gca gcg gag tca ggg gaa cta atc ggg gct tgt gag ttc atg aaa
Ala Ala Glu Ser Gly Glu Leu Ile Gly Ala Cys Glu Phe Met Lys gat cgg tta tat ttt gct act tta agg aat aga cca aaa agc aca gta
Asp Arg Leu Tyr Phe Ala Thr Leu Arg Asn Arg Pro Lys Ser Thr Val aat acc cac tat ttc tcc atc gat gag gag ctg gtc tat gaa aat ttc
Asn Thr His Tyr Phe Ser Ile Asp Glu Glu Leu Val Tyr Glu Asn Phe tat gca gat ttt gga ccg ctg aac ttg gca atg gtg tac aga tat tgc
Tyr Ala Asp Phe Gly Pro Leu Asn Leu Ala Met Val Tyr Arg Tyr Cys tgc aaa cta aac aag aaa cta aaa tca tac agt ttg tca aga aag aaa
Cys Lys Leu Asn Lys Lys Leu Lys Ser Tyr Ser Leu Ser Arg Lys Lys ata gtg cac tac acc tgt ttt gac caa cgg aaa aga gca aat gca gca
Ile Val His Tyr Thr Cys Phe Asp Gln Arg Lys Arg Ala Asn Ala Ala ttt ttg ata ggt gcc tat gca gta atc tat tta aag aag aca cca gaa
Phe Leu Ile Gly Ala Tyr Ala Val Ile Tyr Leu Lys Lys Thr Pro Glu gaa gcc tac aga gca ctc ctg tct ggc tca aac ccc ccc tat ctt cca
Glu Ala Tyr Arg Ala Leu Leu Ser Gly Ser Asn Pro Pro Tyr Leu Pro ttc agg gat gct tcc ttt gga aat tgc act tac aat ctc acc att ctc
Phe Arg Asp Ala Ser Phe Gly Asn Cys Thr Tyr Asn Leu Thr Ile Leu gac tgt ttg cag gga atc aga aag gga tta caa cat gga ttt ttt gac
Asp Cys Leu Gln Gly Ile Arg Lys Gly Leu Gln His Gly Phe Phe Asp ttt gag aca ttt gat gtg gat gaa tat gaa cat tat gag cga gtt gaa
Phe Glu Thr Phe Asp Val Asp Glu Tyr Glu His Tyr Glu Arg Val Glu aat ggt gac ttc aac tgg att gtt cca gga aaa ttt tta gca ttt agt
Asn Gly Asp Phe Asn Trp Ile Val Pro Gly Lys Phe Leu Ala Phe Ser gga cca cat cct aaa agc aaa att gag aat ggt tat cct ctt cac gcc
Gly Pro His Pro Lys Ser Lys Ile Glu Asn Gly Tyr Pro Leu His Ala

Figure 1 cct gaa gcc tac ttt cct tat ttc aaa aag cat aat gtg act gca gtt
Pro Glu Ala Tyr Phe Pro Tyr Phe Lys Lys His Asn Val Thr Ala Val gtg agg cta aac aaa aag att tat gag gca aag cgc ttc aca gac gct
Val Arg Leu Asn Lys Lys Ile Tyr Glu Ala Lys Arg Phe Thr Asp Ala ggc ttc gag cac tat gac ctc ttc ttc ata gat ggc agc aca ccc agt
Gly Phe Glu His Tyr Asp Leu Phe Phe Ile Asp Gly Ser Thr Pro Ser gac aac atc gtg cga agg ttc ctg aac atc tgt gag aac acc gaa ggg
Asp Asn Ile Val Arg Arg Phe Leu Asn Ile Cys Glu Asn Thr Glu Gly gcc atc gcc gtt cac tgc aaa gct ggt ctt gga aga aca ggg aca ttg
Ala Ile Ala Val His Cys Lys Ala Gly Leu Gly Arg Thr Gly Thr Leu ata gcc tgt tat gta atg aaa cac tac agg ttt aca cat gct gaa ata
Ile Ala Cys Tyr Val Met Lys His Tyr Arg Phe Thr His Ala Glu Ile att gct tgg att aga ata tgc cgg cca ggc tct att ata gga ccc cag
Ile Ala Trp Ile Arg Ile Cys Arg Pro Gly Ser Ile Ile Gly Pro Gln cag cac ttc ctg gaa gaa aaa caa gca tcg ttg tgg gtc caa gga gac
Gln His Phe Leu Glu Glu Lys Gln Ala Ser Leu Trp Val Gln Gly Asp att ttc cga tcc aaa ctg aaa aat cga cca tcc agt gaa gga agt att
Ile Phe Arg Ser Lys Leu Lys Asn Arg Pro Ser Ser Glu Gly Ser Ile aat aaa att ctt tct ggc cta gat gat atg tct att ggt gga aat ctt
Asn Lys Ile Leu Ser Gly Leu Asp Asp Met Ser Ile Gly Gly Asn Leu tca aaa aca caa aac atg gaa cga ttt gga    (SEQ ID NO:3)
Ser Lys Thr Gln Asn Met Glu Arg Phe Gly    (SEQ ID NO:2)

Figure 1 (continued)

MODIFIED CDC14 PHOSPHATASE PROTEINS AND CONSTRUCTS FOR IMPROVED EXPRESSION AND PURIFICATION

FIELD OF THE INVENTION

The present invention is in the field of phosphatase proteins, recombinant DNA molecules, and protein production and purification. The present invention provides novel phosphatase polypeptides, encoding nucleic acid molecules, expression constructs/vectors and methods of production thereof, and methods of expressing and purifying phosphatase polypeptides using these constructs/vectors, all of which are useful in the development of human therapeutics and diagnostic compositions and methods.

BACKGROUND OF THE INVENTION

Phosphatase proteins, particularly members of the Cdc14 phosphatase subfamily, are a major target for drug action and development. Accordingly, it is valuable to the field of pharmaceutical development to develop improved Cdc14 nucleic acid constructs for improved expression and purification of Cdc14 proteins. The present invention advances the state of the art by providing novel Cdc14 nucleic acid constructs/vectors and methods of using such constructs/vectors for expressing and purifying modified Cdc14 phosphatase proteins which are expressed as a single form at a high yield and can be readily purified to homogeneity.

Protein Phosphatases

Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of certain residues on proteins. The phosphorylation state of a protein may affect its conformation and/or enzymic activity as well as its cellular location. The phosphorylation state of a protein is modified through the reciprocal actions of protein kinases (PKs) and protein phosphatases (PPs) at various specific amino acid residues.

The protein phosphorylation/dephosphorylation cycle is one of the major regulatory mechanisms employed by eukaryotic cells to control cellular activities. It is estimated that more than 10% of the proteins active in a typical mammalian cell are phosphorylated. The high-energy phosphate that confers activation and is transferred from adenosine triphosphate molecules to proteins by protein kinases is subsequently removed from the proteins by protein phosphatases. In this way, the phosphatases control most cellular signaling events that regulate cell growth and differentiation, cell-to-cell contacts, the cell cycle, and oncogenesis.

Three protein phosphatase families have been identified as evolutionarily distinct. These include the serine/threonine phosphatases, the protein tyrosine phosphatases, and the acid/alkaline phosphatases (Carbonneau H. and Tonks N. K. (1992) Annu. Rev. Cell Biol. 8:463–93).

The serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups, PP-I, PP-IIA, PP-IIB, and PP-IIC.

PP-I dephosphorylates many of the proteins phosphorylated by cylic AMP-dependent protein kinase and is therefore an important regulator of many cyclic AMP mediated, hormone responses in cells. PP-IIA has broad specificity for control of cell cycle, growth and proliferation, and DNA replication and is the main phosphatase responsible for reversing the phosphorylations of serine/threonine kinases. PP-IIB, or calcineurin (Cn), is a Ca.sup.+2-activated phosphatase; it is involved in the regulation of such diverse cellular functions as ion channel regulation, neuronal transmission, gene transcription, muscle glycogen metabolism, and lymphocyte activation.

PP-IIC is a Mg.sup.++-dependent phosphatase which participates in a wide variety of functions including regulating cyclic AMP-activated protein-kinase activity, Ca.sup.++-dependent signal transduction, tRNA splicing, and signal transmission related to heat shock responses. PP-IIC is a monomeric protein with a molecular mass of about 40–45 kDa. One alpha. and several beta. isoforms of PP-IIC have been identified (Wenk, J. et al. (1992) FEBS Lett. 297: 135–138; Terasawa, T. et al. (1993) Arch. Biochem. Biophys. 307: 342–349; and Kato, S. et al. (1995) Arch. Biochem. Biophys. 318: 387–393).

The levels of protein phosphorylation required for normal cell growth and differentiation at any time are achieved through the coordinated action of PKs and PPS. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus, which is characterized by insufficient or a lack of insulin signal transduction, can be caused by any abnormality at any step along the insulin signaling pathway. (Olefsky, 1988, in "Cecil Textbook of Medicine," 18th Ed., 2:1360–81).

It is also well known, for example, that the overexpression of PTKs, such as HER2, can play a decisive role in the development of cancer (Slamon et al., 1987, Science 235: 77–82) and that antibodies capable of blocking the activity of this enzyme can abrogate tumor growth (Drebin et al., 1988, Oncogene 2:387–394). Blocking the signal transduction capability of tyrosine phosphatases such as Flk-1 and the PDGF receptor have been shown to block tumor growth in animal models (Millauer et al., 1994, Nature 367:577; Ueno et al., Science, 252:844–848).

Relatively less is known with respect to the direct role of phosphatases in signal transduction; PPs may play a role in human diseases. For example, ectopic expression of RPTP.alpha. produces a transformed phenotype in embryonic fibroblasts (Zheng et al., Nature 359:336–339), and overexpression of RPTP.alpha. in embryonal carcinoma cells causes the cells to differentiate into a cell type with neuronal phenotype (den Hertog et al., EMBO J 12:3789–3798). The gene for human RPTP.gamma. has been localized to chromosome 3p21 which is a segment frequently altered in renal and small lung carcinoma. Mutations may occur in the extracellular segment of RPTP.gamma. which renders a RPTP that no longer respond to external signals (LaForgia et al., Wary et al., 1993, Cancer Res 52:478–482). Mutations in the gene encoding PTP1C (also known as HCP, SHP) are the cause of the moth-eaten phenotype in mice that suffer severe immunodeficiency, and systemic autoimmune disease accompanied by hyperproliferation of macrophages (Schultz et al., 1993, Cell 73:1445–1454). PTP1D (also known as Syp or PTP2C) has been shown to bind through SH2 domains to sites of phosphorylation in PDGFR, EGFR and insulin receptor substrate 1 (IRS-1). Reducing the activity of PTP1D by microinjection of anti-PTP1D antibody has been shown to block insulin or EGF-induced mitogenesis (Xiao et al., 1994, J Biol Chem 269:21244–21248).

Cdc14 Phosphatases

Cdc14 is a member of the dual-specificity protein tyrosine phosphatase family, and is related to PTEN/MMAC1 (also known as "phosphatase and tensin homolog", "phosphatase and tensin homolog deleted on chromosome 10", and "mutated in multiple advanced cancers 1") (Li et al., *J. Biol. Chem.* 272 (47), 29403–29406 (1997)). The human Cdc14 protein is similar to the yeast (*Saccaromyces cerevisiae*) Cdc14 protein, which has been shown to play important roles in the exit of cell mitosis and initiation of DNA replication and is crucial for cell cycle progression in *Saccaromyces cerevisiae*. The yeast Cdc14 phosphatase regulates the cell cycle by dephosphorylating proteins that have been phosphorylated by the cyclin-dependent kinase Cdc28/clb. In humans, Cdc14 phosphatases have been shown to interact with and dephosphorylate the tumor suppressor protein p53, suggesting that Cdc14 is important in humans for controlling the cell cycle and regulating the function of p53 (Li et al., *J. Biol. Chem.* 275 (4), 2410–2414 (2000)). The human Cdc14A gene has been mapped to human chromosome band 1p21, which is a chromosomal region that has been shown to exhibit loss of heterozygosity in highly differentiated breast carcinoma and malignant mesothelioma (Wong et al., *Genomics* 59 (2), 248–251 (1999)). A 48 bp deletion in the Cdc14A gene has been identified in a breast carcinoma cell line, and loss of expression of the wild-type allele in the breast cancer cell line indicates that Cdc14A may be a tumor suppressor gene that is inactivated during tumorigenesis (Wong et al., *Genomics* 59 (2), 248–251 (1999)).

Because of these important biological functions, Cdc14 phosphatase proteins, and encoding nucleic acid molecules, are well established in the art as having valuable commercial utilities related to cancer and other disorders, such as for developing agents for the prognosis, diagnosis, prevention, and/or treatment of cancer.

The amino acid sequence of the art-known Cdc14, homolog A, isoform 1 protein (referred to herein as "Cdc14A1") is disclosed in Genbank gi:15451929, and the nucleotide sequence of the art-known Cdc14A1 mRNA transcript is disclosed in Genbank gi:15419128. These art-known Cdc14A1 protein and encoding nucleic acid sequences are also disclosed in U.S. Pat. No. 6,331,614 (Wong et al., issued Dec. 18, 2001). References herein to the "native" Cdc14A1 gene/protein are intended to refer to genes/proteins having these art-known sequences.

Further information on the Cdc14 gene/protein, particularly the Cdc14A1 variant, can be found in the following patent and journal articles: U.S. Pat. No. 6,331,614 (Wong et al., issued Dec. 18, 2001); Wong et al., "Genomic structure, chromosomal location, and mutation analysis of the human CDC14A gene", *Genomics* 59 (2), 248–251 (1999); Li et al., "A family of putative tumor suppressors is structurally and functionally conserved in humans and yeast", *J. Biol. Chem.* 272 (47), 29403–29406 (1997); Li et al., "The human Cdc14 phosphatases interact with and dephosphorylate the tumor suppressor protein p53", *J. Biol. Chem.* 275 (4), 2410–2414 (2000); and OMIM entry No. 601728 (for information on PTEN/MMAC1).

Expression and Purification of Phosphatase Proteins

Although it is well recognized in the art that phosphatase proteins, particularly Cdc14 proteins, have valuable commercial and medical utilities due to the important roles that they play in such biological functions as cell cycle regulation and tumorigenesis, it is also recognized that expression and purification of phosphatase proteins such as Cdc14 is problematic. This has hindered the usefulness of phosphatase genes/proteins in the development of therapeutic agents, such as for treating cancer. For example, expression of a phosphatase gene may lead to the production of numerous forms of the phosphatase protein having different molecular weights, and it may be difficult to determine which, if any, of these forms are active phosphatases. Various other impurities may also be co-expressed along with the intended phosphatase protein. For example, the GST portion of a fusion protein may be expressed by itself.

Thus, a need exists in the art for modified phosphatase proteins, and nucleic acid constructs for expressing these proteins, that can be efficiently expressed as a single form of the intended phosphatase with high yield and that can be readily purified to homogeneity, while still retaining the phosphatase activity of the native phosphatase enzyme.

Consequently, the development of modified Cdc14 proteins and nucleic acid expression constructs, and methods of making and using them for improved expression and purification of Cdc14 phosphatase proteins, satisfies a need in the art by providing new compositions and methods that are useful in the development of human therapeutic and diagnostic agents, particularly for cancer.

SUMMARY OF THE INVENTION

The present invention provides modified Cdc14 proteins, particularly novel modifications of the human Cdc14A1 phosphatase enzyme. In a preferred modification, termed Cdc14AS, the sequence C-terminal to the catalytic domain has been deleted. This modification results in high levels of expression of a single form of the enzyme, which retains the phosphatase activity of the native Cdc14A1 enzyme, thereby enabling purification of a homogeneous preparation of active enzyme at a high yield. The present invention provides amino acid sequences of a modified Cdc14AS phosphatase enzyme, nucleic acid sequences of nucleic acid molecules that encode the modified Cdc14AS phosphatase, constructs/vectors for expressing the protein, host cells containing the constructs/vectors, methods of making and using the constructs, and methods of expressing and purifying the modified Cdc14AS phosphatase enzyme. These novel protein sequences, nucleic acid molecules, and constructs/vectors and host cells that express these proteins, are useful in the development of human therapeutic and diagnostic agents, such as pharmaceutical compounds that modulate phosphatase activity in cells and tissues that express the Cdc14 phosphatase.

DESCRIPTION OF THE FIGURE

The FIGURE provides the following:

1) a preferred amino acid sequence (SEQ ID NO:1) of the preferred Cdc14AS fusion protein, including an N-terminal His-tag and S-tag (which may be acquired from a vector such as the pET-30a vector) The amino acid residues representing the heterologous His-tag and S-tag are italicized (residues 1–52 of SEQ ID NO:1). Residues 53–429 of SEQ ID NO:1 are identical to SEQ ID NO:2.

2) amino acid residues 2–378 (shown in SEQ ID NO:2 as residues 1–377) of the native Cdc14A1 phosphatase disclosed in Genbank gi:15451929 and U.S. Pat. No. 6,331, 614, with the encoding nucleic acid sequence (SEQ ID NO:3).

[SEQ ID NO:3 corresponds to nucleotides 4–1134 (shown in SEQ ID NO:3 as residues 1–1131) of the protein-coding (CDS) region of the native Cdc14A1 gene/mRNA transcript disclosed in Genbank gi:15451928 and U.S. Pat. No. 6,331, 614 (furthermore, residues 4–1134 of the CDS region of Genbank gi:15451928 correspond to residues 469–1599 of the overall 4262 bp sequence of Genbank gi:15451928)].

DETAILED DESCRIPTION OF THE INVENTION

General Description

The present invention is based on the development of modified phosphatase proteins, referred to herein as "Cdc14AS" phosphatases, encoding nucleic acid molecules, constructs/vectors and host cells for expressing these modified phosphatase proteins, and methods of making and using these novel compositions. These novel modified phosphatase proteins and expression constructs enable high levels of expression of a single form of the Cdc14 protein that retains the phosphatase activity of native Cdc14 phosphatases, particularly the native Cdc14A1 phosphatase, thereby allowing the protein to be readily purified to homogeneity while retaining it's activity. Thus, the invention satisfies a need in the art for more efficient means for expressing and purifying phosphatase enzymes, particularly Cdc14 phosphatase enzymes.

Relative to the native Cdc14A1 protein, preferred embodiments of the Cdc14AS variant have the sequence C-terminal to the catalytic domain deleted. This modification results in the expression of a single form of the enzyme enabling purification of a homogeneous preparation of active enzyme at a high yield.

Briefly, in preferred embodiments, the 5' sequence of the human Cdc14A1 gene, extending from nucleotides 4 to 1134 of the protein-coding region of the gene (SEQ ID NO:3), is obtained (e.g., by PCR amplification from a nucleic acid sample such as a cDNA library or whole genomic DNA) and cloned into the EcoRI/NotI sites of a pET-30a vector to yield a construct for expression of a C-terminal truncated variant of Cdc14A1 (termed Cdc14AS). This construct expresses residues 2 to 378 of Cdc14A1 (SEQ ID NO:2) as a fusion protein with an N-terminal His-tag and S-tag of the pET-30a vector (SEQ ID NO:1). Once created, the construct can be maintained and used repeatedly to express modified Cdc14 proteins such as Cdc14AS, without the need to re-create the construct. A detailed description of preferred methods for creating a Cdc14AS expression construct and for expressing and purifying Cdc14AS proteins is provided in the Examples section at the end of the Description of the Invention.

Heterologous nucleic acid sequences encoding heterologous polypeptides, such as His-tags and S-tags, are well known in the art. Such heterologous nucleic acid sequences can be provided in commercially available vectors. For example, in preferred embodiments, a pET-30 expression vector (Novagen), most preferably a pET-30a expression vector, which encodes a heterologous protein sequence, is used to form the preferred Cdc14AS protein sequence [see SEQ ID NO:1 in the FIGURE, in which the heterologous portion (residues 1–52) of the protein is italicized; this heterologous portion is preferably obtained from a pET-30 vector such as the pET-30a vector]. The pET-30a–c vectors (Novagen) provide a His-tag and S-tag as part of an N-terminal His-tag/thrombin/S-tag/enterokinase configuration (the vectors also comprise an optional C-terminal His-tag sequence). In other embodiments, however, other heterologous protein sequences may be used in addition to, or instead of, the His-tag and/or S-tag, and heterologous nucleic acid sequences that encode heterologous protein sequences may be acquired from a wide variety of sources. Such sources include, for example, vectors from a wide variety of commercial manufacturers, plasmid vectors other than pET-30 vectors, vectors other than plasmids, and non-vector sources known in the art. In yet other embodiments, no heterologous sequence is used.

The present invention provides amino acid sequences (SEQ ID NOS:1–2) of these Cdc14AS phosphatase proteins, nucleic acid sequences (SEQ ID NO:3) encoding these proteins, constructs/vectors and host cells for expressing these modified phosphatase proteins, methods of making and using the constructs/vectors, and methods of expressing and purifying the modified Cdc14AS enzymes.

The art has clearly established the commercial importance of members of the phosphatase family of proteins, particularly Cdc14 phosphatase proteins, as well as the need for more efficient means for expressing such proteins. Some of the more specific features of the polypeptides, nucleic acid molecules, and constructs/vectors and host cells of the present invention, and the uses thereof, are described herein, particularly in the Background of the Invention and in the FIGURE, and/or are known within the art for members of the Cdc14 subfamily of phosphatase proteins.

Specific Embodiments

Peptide Molecules

The present invention provides modified Cdc14 proteins. In particular, amino acid sequences of a preferred modification of the Cdc14A1 phosphatase protein, termed Cdc14AS, in which the sequence C-terminal to the catalytic domain has been deleted, are provided. This modification results in the expression of a single form of the enzyme enabling purification of a homogeneous preparation of active enzyme at a high yield (preferred Cdc14AS protein sequences and encoding nucleic acid sequences are provided in the FIGURE). The peptide sequences provided in the FIGURE (SEQ ID NOS:1-2), as well as obvious variants described herein and apparent to one of ordinary skill in the art, including allelic variants, will be referred to herein as the phosphatase polypeptides/peptides/proteins/enzymes of the present invention, phosphatase polypeptides/peptides/proteins/enzymes, Cdc14AS polypeptides/peptides/proteins/enzymes, Cdc14 polypeptides/peptides/proteins/enzymes of the present invention, polypeptides/peptides/proteins/enzymes of the present invention, or molecules of the present invention. The terms "protein(s)", "peptide(s)", and "polypeptide(s)" are used herein interchangeably.

The present invention provides isolated peptide molecules that consist of, consist essentially of, or comprise the amino acid sequences of the phosphatase peptides disclosed in the FIGURE, as well as all obvious variants of these peptides that are within the art to make and use. Some of these variants are described below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phosphatase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phosphatase peptide can be purified from cells that naturally express it, purified from cells that have been altered to express it (recombinant), or synthesized using known protein synthesis methods. For example, a nucleic acid molecule encoding the phosphatase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in the FIGURE (SEQ ID NOS:1–2), for example, proteins encoded by the nucleic acid sequences shown in the FIGURE (SEQ ID NO:3). A protein consists of an amino acid sequence when the amino acid sequence is the final amino acid sequence of the protein.

The present invention further provides proteins that consist essentially of the amino acid sequences provided in the FIGURE (SEQ ID NOS:1–2), for example, proteins encoded by the nucleic acid sequences shown in the FIGURE (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in the FIGURE (SEQ ID NOS:1–2), for example, proteins encoded by the nucleic acid sequences shown in the FIGURE (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. It is understood, however, that the proteins contemplated by the present invention that comprise the amino acid sequences provided in the FIGURE (SEQ ID NOS:1–2) exclude proteins disclosed prior to the present invention.

A brief description of how various types of these proteins can be made/isolated is provided below. A detailed description of a preferred method for making and purifying Cdc14AS proteins is provided in the Examples section at the end of the Description of the Invention.

The phosphatase peptides of the present invention can be attached to heterologous sequences to form chimeric or fusion proteins. Such chimeric and fusion proteins comprise a phosphatase peptide operatively linked to a heterologous protein having an amino acid sequence not substantially homologous to the phosphatase peptide. "Operatively linked" indicates that the phosphatase peptide and the heterologous protein are fused in-frame. The heterologous protein can be fused to the N-terminus or C-terminus of the phosphatase peptide.

In some uses, the fusion protein does not affect the activity of the phosphatase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phosphatase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A phosphatase peptide-encoding nucleic acid can be cloned into such an expression vector such that the fusion moiety is linked in-frame to the phosphatase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the present invention.

Such variants can readily be identified/made using molecular techniques and the sequence information disclosed herein. Further, such variants can readily be distinguished from other peptides based on sequence and/or structural homology to the phosphatase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phosphatase peptides of the present invention as well as being encoded by the same genetic locus as the phosphatase peptide provided herein. The Cdc14A gene maps to human chromosome band 1p21.

Allelic variants of a phosphatase peptide can readily be identified as being a human protein having a high degree (significant) of sequence homology/identity to at least a portion of the phosphatase peptide as well as being encoded by the same genetic locus as the phosphatase peptide provided herein. The Cdc14A gene maps to human chromosome band 1p21. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phosphatase peptide-encoding nucleic acid molecule under stringent conditions as more fully described below.

Paralogs of a phosphatase peptide can readily be identified as having some degree of significant sequence homology/identity to at least a portion of the phosphatase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phosphatase peptide-encoding nucleic acid molecule under moderate to stringent conditions as more fully described below.

Orthologs of a phosphatase peptide can readily be identified as having some degree of significant sequence homology/identity to at least a portion of the phosphatase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phosphatase peptide-encoding nucleic acid molecule under moderate to stringent conditions, as more fully described below, depending on the degree of relatedness of the two organisms yielding the proteins.

Non-naturally occurring variants of the phosphatase peptides of the present invention can readily be generated using recombinant techniques. Such variants include, but are not limited to deletions, additions and substitutions in the amino acid sequence of the phosphatase peptide. For example, one class of substitutions is conserved amino acid substitutions. Such substitutions are those that substitute a given amino acid in a phosphatase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phosphatase peptides can be fully functional or can lack function in one or more activities, e.g. ability to bind substrate, ability to dephosphorylate substrate, ability to mediate signaling, etc. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the sequences provided in the FIGURE. The latter procedure introduces single alanine mutations at every residue in the molecule. The resulting mutant molecules are then tested for biological activity such as phosphatase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255: 306–312 (1992)).

The present invention further provides fragments of the phosphatase peptides, in addition to proteins and peptides that comprise and consist of such fragments, particularly those comprising the residues identified in the FIGURE. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phosphatase peptide. Such fragments can be chosen based on the ability to retain one or more of the biological activities of the phosphatase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phosphatase peptide, e.g., active site, a transmembrane domain or a substrate-binding domain. Further, possible fragments include, but are not limited to, domain- or motif-containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phosphatase peptides are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the phosphatase peptides of the present invention also encompass derivatives or analogs in which a substituted amino acid residue is not one encoded by the genetic code, in which a substituent group is included, in which the mature phosphatase peptide is fused with another compound, such as a compound to increase the half-life of the phosphatase peptide, or in which the additional amino acids are fused to the mature phosphatase peptide, such as a leader or secretory sequence or a sequence for purification of the mature phosphatase peptide or a pro-protein sequence.

Protein/Peptide Uses

The uses of the proteins preferably involve utilization of a modified Cdc14 phosphatase protein as disclosed herein, most preferably the Cdc14AS phosphatase or an obvious variant thereof, for investigation of native Cdc14 phosphatases.

The proteins of the present invention can be used in substantial and specific assays related to phosphatase function; to raise antibodies or to elicit another immune response; as a reagent (including the labeled reagent) in assays designed to quantitatively determine levels of the native protein (or its binding partner, substrate, or ligand) in biological fluids; and as markers for tissues in which the corresponding native protein is preferentially expressed (either constitutively or at a particular stage of tissue differentiation or development or in a disease state). Where the protein binds or potentially binds to another protein, substrate, or ligand (such as, for example, in a phosphatase-effector protein interaction or phosphatase-substrate interaction), the protein can be used to identify the binding partner/ligand/substrate so as to develop a system to identify inhibitors of the binding interaction. Any or all of these uses are capable of being developed into reagent grade or kit format for commercialization as commercial products.

The assays preferably utilize the Cdc14AS phosphatase disclosed herein, or an obvious variant thereof, for investigating native Cdc14 phosphatases, such as for developing pharmaceutical compounds, antibodies, or other agents that interact with native Cdc14 phosphatases.

Methods for performing the exemplary uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phosphatases isolated from humans and their human/mammalian orthologs serve as targets for identifying agents for use in mammalian therapeutic applications, e.g. a human drug, particularly in modulating a biological or pathological response in a cell or tissue that expresses the phosphatase. A large percentage of pharmaceutical agents are being developed that modulate the activity of phosphatase proteins, particularly members of the Cdc14 subfamily (see Background of the Invention). The structural and functional information provided in the Background and the FIGURE provides specific and substantial uses for the molecules of the present invention. Such uses can readily be determined using the information provided herein, that which is known in the art, and routine experimentation.

The proteins of the present invention (including variants and fragments that may have been disclosed prior to the present invention) are useful for biological assays related to phosphatases that are related to members of the Cdc14 subfamily. Such assays involve any of the known phosphatase functions or activities or properties useful for diagnosis and treatment of phosphatase-related conditions that are specific for the subfamily of phosphatases that the one of the present invention belongs to, particularly in cells and tissues that express the phosphatase. The assays preferably utilize the Cdc14AS phosphatase disclosed herein for evaluating functions or activities or properties of native Cdc14 phosphatases.

The proteins of the present invention are also useful in drug screening assays, in cell-based or cell-free systems. Cell-based systems can be native, i.e., cells that normally express the phosphatase, as a biopsy or expanded in cell culture. In an alternate embodiment, cell-based assays involve recombinant host cells expressing the phosphatase protein. The drug screening assays preferably utilize the Cdc14AS phosphatase disclosed herein for screening drugs that bind or otherwise interact or modulate native Cdc14 phosphatases.

The polypeptides can be used to identify compounds that modulate phosphatase activity of the protein in its natural state or an altered form that causes a specific disease or pathology associated with the phosphatase. Both the phosphatases of the present invention and appropriate variants and fragments can be used in high-throughput screens to assay candidate compounds for the ability to bind to the phosphatase. These compounds can be further screened against a functional phosphatase to determine the effect of the compound on the phosphatase activity. Further, these compounds can be tested in animal or invertebrate systems to determine activity/effectiveness. Compounds can be identified that activate (agonist) or inactivate (antagonist) the phosphatase to a desired degree.

Further, the proteins of the present invention can be used to screen a compound for the ability to stimulate or inhibit interaction between the phosphatase protein and a molecule that normally interacts with the native phosphatase protein, e.g. a substrate or a component of the signal pathway that the native phosphatase protein normally interacts (for example, a substrate that is phosphorylated by a kinase and dephosphorylated by the native phosphatase). Such assays typically include the steps of combining the phosphatase protein with a candidate compound under conditions that allow the phosphatase protein, or fragment, to interact with the target molecule, and to detect the formation of a complex between the protein and the target or to detect the biochemical consequence of the interaction with the phosphatase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phosphatases or appropriate fragments containing mutations that affect phosphatase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phosphatase activity. The assays typically involve an assay of events in the signal transduction pathway that indicate phosphatase activity. Thus, the dephosphorylation of a substrate, activation of a protein, a change in the expression of genes that are up- or down-regulated in response to the phosphatase protein-dependent signal cascade can be assayed.

Any of the biological or biochemical functions mediated by the phosphatase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Specification and FIGURE. Specifically, a biological function of a cell or tissues that expresses the phosphatase can be assayed.

Binding and/or activating compounds can also be screened by using chimeric phosphatase proteins in which an amino terminal extracellular domain, or parts thereof, an entire transmembrane domain or subregions, such as any transmembrane segments or any intracellular or extracellular loops and a carboxy terminal intracellular domain, or parts thereof, can be replaced by heterologous domains or subregions. For example, a substrate-binding region can be used that interacts with a different substrate then that which is recognized by the native phosphatase. Accordingly, a different set of signal transduction components is available as an end-point assay for activation. This allows for assays to be performed in other than the specific host cell from which the phosphatase is derived.

The proteins of the present invention are also useful in competition binding assays in methods designed to discover compounds that interact with the phosphatase (e.g., binding partners, substrates, and/or ligands). Thus, a compound is exposed to a phosphatase polypeptide under conditions that allow the compound to bind or to otherwise interact with the polypeptide. Soluble polypeptide is also added to the mixture. If the test compound interacts with the soluble polypeptide, it decreases the amount of complex formed or activity from the phosphatase target. This type of assay is particularly useful in cases in which compounds are sought that interact with specific regions of the phosphatase. Thus, the soluble polypeptide that competes with the target phosphatase region is designed to contain peptide sequences corresponding to the region of interest.

To perform cell free drug screening assays, it is sometimes desirable to immobilize either the phosphatase protein (e.g., the Cdc14AS protein), or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phosphatase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphatase-binding protein and a candidate compound are incubated in the phosphatase protein-presenting wells and the amount of complex trapped in the well can be quantitated. Methods for detecting such complexes, in addition to those described above for the GST-immobilized complexes, include immunodetection of complexes using antibodies reactive with the phosphatase protein target molecule, or which are reactive with phosphatase protein and compete with the target molecule, as well as enzyme-linked assays which rely on detecting an enzymatic activity associated with the target molecule.

Agents that modulate one of the phosphatases of the present invention can be identified using one or more of the above assays, alone or in combination. The above assays preferably utilize the Cdc14AS phosphatase disclosed herein for investigating native Cdc14 phosphatases. It is generally preferable to use a cell-based or cell free system first and then confirm activity in an animal or other model system. Such model systems are well known in the art and can readily be employed in this context.

Modulators of phosphatase protein activity identified according to these drug-screening assays can be used to treat a subject with a disorder mediated by the phosphatase pathway, by treating cells or tissues that express the native phosphatase. These methods of treatment include the steps of administering a modulator of phosphatase activity in a pharmaceutical composition to a subject in need of such treatment, the modulator being identified as described herein.

In yet another aspect of the invention, the phosphatase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the phosphatase and are involved in phosphatase activity. Such phosphatase-binding proteins are also likely to be involved in the propagation of signals by the phosphatase proteins or phosphatase targets as, for example, downstream elements of a phosphatase-mediated signaling pathway. Alternatively, such phosphatase-binding proteins are likely to be phosphatase inhibitors.

The two-hybrid system is based on the modular nature of most transcription factors, which consist of separable DNA-binding and activation domains. Briefly, the assay utilizes two different DNA constructs. In one construct, the gene that codes for a phosphatase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phosphatase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phosphatase protein.

This invention further pertains to novel agents identified by the above-described screening assays. Accordingly, it is within the scope of this invention to further use an agent identified as described herein in an appropriate animal model. For example, an agent identified as described herein (e.g., a phosphatase-modulating agent, an antisense phosphatase nucleic acid molecule, a phosphatase-specific antibody, or a phosphatase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phosphatase proteins of the present invention are also useful to provide a target for diagnosing a disease or predisposition to disease mediated by the native peptide. Accordingly, the presence, or levels of, the native protein (or encoding mRNA) can be detected in a cell, tissue, or organism. The method involves contacting a biological sample with a compound capable of interacting with the phosphatase protein such that the interaction can be detected. Such an assay can be provided in a single detection format or a multi-detection format such as an antibody chip array. The assays preferably utilize the Cdc14AS phosphatase disclosed herein for identifying compounds that interact with native Cdc14 phosphatases.

One agent for detecting a protein in a sample is an antibody capable of selectively binding to a target protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phosphatase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), arid Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphatase protein in which one or more of the phosphatase functions in one population are different from those in another population. The peptides thus allow a target to ascertain a genetic predisposition that can affect treatment modality. Thus, for example, in a ligand-based treatment, polymorphisms may give rise to amino terminal extracellular domains and/or other substrate-binding regions that are more or less active in substrate binding, and phosphatase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the native protein. Accordingly, methods for treatment include the use of the phosphatase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as a phosphatase catalytic domain, and domains of sequence homology or divergence amongst the family, such as those that can readily be identified using protein alignment methods using the sequences presented in the FIGURE.

Antibodies are preferably prepared from regions or discrete fragments of the phosphatase proteins. Antibodies can be prepared from any region of the peptide as described herein. However, preferred regions will include those involved in function/activity and/or phosphatase-substrate (or other binding partner) interaction. The sequences provided in the FIGURE can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected based on a physical property, such as fragments corresponding to regions that are located on the surface of the protein, e.g., hydrophilic regions or can be selected based on sequence uniqueness.

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The uses of the antibodies preferably involve utilization of antibodies that interact with a modified Cdc14 phosphatase as disclosed herein, most preferably the Cdc14AS phosphatase or an obvious variant thereof, for investigation of native Cdc14 phosphatases or antibodies thereto.

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of a native protein in cells or tissues to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition.

Further, the antibodies can be used to assess expression in disease states such as in active stages of the disease or in an individual with a predisposition toward disease related to the protein's function. When a disorder is caused by inappropriate tissue distribution, developmental expression, level of expression of the native protein or an expressed/processed form, the antibody can be prepared against the normal protein. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. The diagnostic uses can be applied, not only in genetic testing, but also in monitoring a treatment modality. Accordingly, where treatment is ultimately aimed at correcting the expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as immunological markers for aberrant protein analyzed by electrophoretic mobility, isoelectric point, tryptic peptide digest, and other physical assays known to those in the art.

The antibodies are also useful for tissue typing. Thus, where a specific native protein has been correlated with expression in a specific tissue, antibodies that are specific for this protein can be used to identify a tissue type.

The antibodies are also useful for inhibiting protein function, for example, blocking the binding of the phosphatase peptide to a binding partner such as a substrate. These uses can also be applied in a therapeutic context in which treatment involves inhibiting the protein's function. An antibody can be used, for example, to block binding, thus modulating (agonizing or antagonizing) the peptide's activity. Antibodies can be prepared against specific fragments containing sites required for function or against intact protein that is associated with a cell or cell membrane.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode modified phosphatase proteins. These isolated nucleic acid molecules can be used in expression constructs/vectors for the expression and subsequent purification of modified phosphatase proteins such as the Cdc14AS phosphatase protein. As previously described, the Cdc14AS protein is a preferred modification of the native Cdc14A1 protein in which the sequence C-terminal to the catalytic domain has been deleted. In preferred embodiments, the 5' sequence of the human Cdc14A1 gene, extending from nucleotides 4 to 1134 of the protein-coding region of the gene (SEQ ID NO:3), is obtained (e.g., by amplifying the region from a nucleic acid sample such as a cDNA library) and cloned into a vector (e.g., a pET-30 vector, preferably a pET-30a vector) to form a construct for expression of Cdc14AS. Once created, the construct can be maintained and used repeatedly for protein expression, without the need to re-create the construct. This construct expresses residues 2 to 378 (SEQ ID NO:2) of Cdc14A1 as a fusion protein in which the sequence C-terminal to the catalytic domain is truncated. The amino acid sequence of a preferred Cdc14AS fusion protein with an N-terminal His-tag and S-tag (such tags may be provided by, for example, a pET-30a vector) is shown in the FIGURE (SEQ ID NO:1). This modification results in the expression of a single form of the enzyme enabling purification of a homogeneous preparation of active enzyme at a high yield.

The nucleic acid molecules of the present invention will consist of, consist essentially of, or comprise a nucleotide sequence that encodes one of the modified phosphatase peptides of the present invention, particularly the Cdc14AS variant, or an allelic variant, ortholog or paralog thereof, or any other obvious variant thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically. Isolated nucleic acid molecules also include amplicons, i.e., nucleic acid molecules that have been amplified, such as by using PCR.

Accordingly, the present invention provides nucleic acid molecules that consist of the nucleotide sequences shown in the FIGURE (SEQ ID NO:3), or any nucleic acid molecule that encodes a protein provided in the FIGURE (SEQ ID NOS:1–2). A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in the FIGURE (SEQ ID NO:3), or any nucleic acid molecule that encodes a protein provided in the FIGURE (SEQ ID NOS:1–2). A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in the FIGURE (SEQ ID NO:3), or any nucleic acid molecule that encodes a protein provided in the FIGURE (SEQ ID NOS: 1–2). A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. It is understood, however, that the nucleic acid molecules contemplated by the present invention that comprise the nucleotide sequences provided in the FIGURE (SEQ ID NO:3) exclude nucleic acid molecules disclosed prior to the present invention.

A brief description of how various types of these nucleic acid molecules can be readily made/isolated is provided below. A detailed description of a preferred method for making a construct comprising a nucleic acid molecule having a nucleotide sequence provided in the FIGURE (SEQ ID NO:3), for expressing the Cdc14AS protein, is provided in the Examples section at the end of the Description of the Invention.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phosphatase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning (including, e.g., PCR amplification-based cloning techniques) or produced by chemical synthetic techniques, or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the phosphatase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in the FIGURE. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents.

A fragment comprises a contiguous nucleotide sequence of about 12 or more nucleotides in length. Further, a fragment could be at least about 20, 30, 40, 50, 100, 250 or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to a nucleotide sequence shown in the FIGURE or a fragment thereof. Such nucleic acid molecules can readily be identified as being able to hybridize under moderate to stringent conditions to a nucleotide sequence shown in the FIGURE or a fragment thereof. Allelic variants can readily be determined by genetic locus of the encoding gene. The Cdc14A gene maps to human chromosome band 1p21.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The uses of the nucleic acid molecules preferably involve utilization of nucleic acid molecules encoding a modified Cdc14 phosphatase as disclosed herein, most preferably the Cdc14AS phosphatase or an obvious variant thereof, for investigation of native Cdc14 phosphatases, or encoding nucleic acid molecules, such as a native Cdc14 gene.

The nucleic acid molecules of the present invention are useful for probes, primers, chemical intermediates, and in biological assays. The nucleic acid molecules are useful as hybridization probes for messenger RNA, transcript/cDNA and genomic DNA to isolate full-length cDNA and genomic clones encoding the peptide shown in the FIGURE and to isolate cDNA and genomic clones that correspond to variants (alleles, orthologs, etc.) that encode the same or related peptides shown in the FIGURE.

The probe can correspond to any sequence along the entire length of the nucleic acid molecules provided in the FIGURE. Accordingly, it could be derived from 5' noncoding regions, the coding region, and 3' noncoding regions.

However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The Cdc14A gene maps to human chromosome band 1p21.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of native nucleic acid expression. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phosphatase protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a phosphatase protein, such as by measuring the level of a phosphatase-encoding nucleic acid in a sample of cells from a subject e.g., mRNA or genomic DNA, or determining if a phosphatase gene has been mutated.

Nucleic acid expression assays are useful for drug screening to identify compounds that modulate phosphatase nucleic acid expression. The nucleic acid expression assays preferably utilize nucleic acid molecules encoding the Cdc14AS phosphatase disclosed herein for identifying compounds that modulate the expression of native Cdc14 phosphatases.

The invention thus provides a method for identifying a compound that can be used to treat a disorder associated with nucleic acid expression of the phosphatase gene, particularly biological and pathological processes that are mediated by the native phosphatase in cells and tissues that express it. The method typically includes assaying the ability of the compound to modulate the expression of the phosphatase nucleic acid and thus identifying a compound that can be used to treat a disorder characterized by undesired phosphatase nucleic acid expression. The assays can be performed in cell-based and cell-free systems. Cell-based assays include cells naturally expressing the phosphatase nucleic acid or recombinant cells genetically engineered to express specific nucleic acid sequences. The assays preferably utilize nucleic acids encoding the Cdc14AS phosphatase disclosed herein for identifying compounds that modulate the expression of native Cdc14 phosphatases.

The assay for phosphatase nucleic acid expression can involve direct assay of nucleic acid levels, such as mRNA levels, or on collateral compounds involved in the signal pathway. Further, the expression of genes that are up- or down-regulated in response to the phosphatase protein signal pathway can also be assayed. In this embodiment the regulatory regions of these genes can be operably linked to a reporter gene such as luciferase.

Thus, modulators of phosphatase gene expression can be identified in a method wherein a cell is contacted with a candidate compound and the expression of mRNA determined. The level of expression of phosphatase mRNA in the presence of the candidate compound is compared to the level of expression of phosphatase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phosphatase nucleic acid expression in cells and tissues that express the native phosphatase. Modulation includes either up-regulation (i.e. activation or agonization) or down-regulation (suppression or antagonization) of nucleic acid expression.

Alternatively, a modulator for phosphatase nucleic acid expression can be a small molecule or drug identified using the screening assays described herein as long as the drug or small molecule modulates phosphatase nucleic acid expression in the cells and tissues that express the native protein.

The nucleic acid molecules are also useful for monitoring the effectiveness of modulating compounds on the expression or activity of the phosphatase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in native phosphatase nucleic acid expression, and particularly in qualitative changes that lead to pathology. The nucleic acid molecules can be used to detect mutations in phosphatase genes and gene expression products such as mRNA. The nucleic acid molecules can be used as hybridization probes to detect naturally occurring genetic mutations in the phosphatase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphatase gene associated with a dysfunction provides a diagnostic tool for an active disease or susceptibility to disease when the disease results from overexpression, underexpression, or altered expression of a phosphatase protein.

Individuals carrying mutations in the phosphatase gene can be detected at the nucleic acid level by a variety of techniques. The Cdc14A gene maps to human chromosome band 1p21. Genomic DNA can be analyzed directly or can be amplified by PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic DNA, mRNA or both) from the cells of the sample, contacting the nucleic acid sample with one or more primers which specifically hybridize to the gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phosphatase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phosphatase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that, while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phosphatase gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phosphatase gene expression in cells, tissues, and organisms. An antisense nucleic acid molecule is generally designed to be complementary to a region of mRNA expressed by the gene so that the antisense molecule can hybridize to the mRNA and thereby block translation of mRNA into protein. Alternatively, an antisense nucleic acid molecule can hybridize to a region of the gene involved in transcription in order to block transcription. Antisense technology is well established in the art and extensively reviewed in *Antisense Drug Technology: Principles, Strategies, and Applications*, Crooke (ed.), Marcel Dekker, Inc.: New York (2001).

Thus, a class of antisense molecules can be used to inactivate mRNA in order to decrease expression of phosphatase-encoding nucleic acid. Accordingly, these molecules can treat a disorder characterized by abnormal or undesired phosphatase nucleic acid expression. This technique generally involves cleavage by means of ribozymes containing nucleotide sequences complementary to one or more regions in the mRNA that attenuate the ability of the mRNA to be translated or that correspond to important functional domains of the encoded protein. Possible regions include, for example, coding regions and particularly coding regions corresponding to the catalytic and other functional activities of the phosphatase protein, such as substrate binding.

The nucleic acid molecules also provide vectors for gene therapy in patients containing cells that are aberrant in phosphatase gene expression. Thus, recombinant cells, which include the patient's cells that have been engineered ex vivo and returned to the patient, are introduced into an individual where the cells produce the desired phosphatase protein to treat the individual.

The invention also encompasses kits for detecting the presence of a native phosphatase nucleic acid in a biological sample. For example, the kit can comprise reagents such as a labeled or labelable nucleic acid or agent capable of detecting phosphatase nucleic acid in a biological sample; means for determining the amount of phosphatase nucleic acid in the sample; and means for comparing the amount of phosphatase nucleic acid in the sample with a standard. The compound or agent can be packaged in a suitable container. The kit can further comprise instructions for using the kit to detect phosphatase protein, mRNA, or DNA.

Nucleic Acid Arrays

The present invention further provides nucleic acid detection kits, such as arrays or microarrays of nucleic acid molecules that are based on the sequence information provided in the FIGURE (SEQ ID NO:3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7-20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million or more. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number greater than two which lends itself to the efficient use of commercially available instrumentation.

A preferred method for conducting sample analysis using a microarray or detection kit is as follows. The RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phosphatase proteins/peptides of the present invention. The methods preferably utilize arrays comprising nucleic acids encoding a modified Cdc14 phosphatase as disclosed herein, most preferably the Cdc14AS phosphatase. In detail, such methods comprise incubating a test sample with one or more nucleic acid molecules and assaying for binding of the nucleic acid molecule with components within the test sample. Such assays will typically involve arrays comprising many nucleic acids, at least one of which is a nucleic acid encoding a modified phosphatase of the present invention, preferably encoding the Cdc14AS phosphatase, and/or alternative alleles or obvious variants thereof.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein.

Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples may include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one or more nucleic acid molecules that can bind to a nucleic acid molecule disclosed herein; and (b) one or more other containers comprising wash reagents and/or reagents capable of detecting presence of a bound nucleic acid.

In detail, a compartmentalized kit includes any kit in which reagents are contained in separate containers. Such containers include, for example, small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the novel nucleic acid molecules of the present invention can be routinely identified using the sequence information disclosed herein and can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, possible vectors may include, for example, a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region, a ribosome-binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include; but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting, for example, as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophosphatase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301– 315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein., (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae*, include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found, for example, in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include, for example, prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In cases in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include, for example, kanamycin-, tetracycline-, or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain-containing proteins, appropriate secretion signals are incorporated into the vector. The signal sequence can be endogenous to the peptides or heterologous to these peptides.

Where the peptide is not secreted into the medium, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that, depending upon the host cell used in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and Host Cells

The uses of the vectors and host cells containing the vectors preferably involve utilization of vectors that express a modified Cdc14 phosphatase as disclosed herein, most preferably the Cdc14AS phosphatase or an obvious variant thereof, as a means of investigating native Cdc14 phosphatases. As discussed previously, the Cdc14AS phosphatase disclosed herein is an improvement over prior art Cdc14 phosphatases in that it can readily be expressed in high yields as a single form of the enzyme with minimal or no impurities, and can readily be purified to homogeneity.

The recombinant host cells expressing the peptides described herein have a variety of uses. First, the cells are useful for producing a phosphatase protein or peptide that can be further purified to produce desired amounts of phosphatase protein or fragments. Thus, host cells containing expression vectors are useful for peptide production. In particular, as described earlier, the novel vectors/constructs described herein, and host cells containing these vectors/constructs, express modified Cdc14 phosphatase proteins, especially Cdc14AS and obvious variants thereof, and are improvements over the prior art in that they enable expression of a single form of a phosphatase enzyme (e.g., the Cdc14AS variant), which retains the phosphatase activity of native phosphatases, and facilitate purification of a homogeneous preparation of active enzyme at a high yield.

Host cells are also useful for conducting cell-based assays involving the phosphatase protein or phosphatase protein fragments, such as those described above as well as other formats known in the art., Thus, a recombinant host cell expressing a phosphatase protein (e.g., the Cdc14AS phosphatase protein) is useful for assaying compounds that stimulate or inhibit phosphatase protein function.

Host cells are also useful for identifying phosphatase protein mutants in which these functions are affected. If the mutants naturally occur and give rise to a pathology, host cells containing the mutations are useful to assay compounds that have a desired effect on the mutant phosphatase protein (for example, stimulating or inhibiting function) which may not be indicated by their effect on the native phosphatase protein. Preferably, vectors/constructs can be produced in which a modified Cdc14 protein (e.g., having a C-terminal truncation), preferably the Cdc14AS protein, having the naturally occurring mutants incorporated therein is expressed, thereby allowing the mutants to be investigated by using the modified Cdc14 protein which, as discussed previously, has improved expression and purification characteristics relative to, for example, the native Cdc14A1 phosphatase.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a phosphatase protein and identifying and evaluating modulators of phosphatase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection or retroviral infection, and allowing the oocyte to develop in a pseudopregnant female foster animal. Any of the phosphatase protein-encoding nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phosphatase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is generally required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to a morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, phosphatase protein activity, and signal transduction, may not be evident from in vitro cell-free or cell-based assays. Accordingly, it is useful to provide non-human transgenic animals to assay in vivo phosphatase protein function, including substrate interaction, the effect of specific mutant phosphatase proteins on phosphatase protein function and substrate interaction, and the effect of chimeric phosphatase proteins. It is also possible to assess the effect of null mutations, i.e., mutations that substantially or completely eliminate one or more phosphatase protein functions.

EXAMPLES

The following is a detailed description of a preferred method for creating Cdc14AS constructs, and for expressing and purifying Cdc14AS proteins.

Creation of a Cdc14AS Construct:

A nucleic acid sample was subjected to PCR (polymerase chain reaction) amplification with the following primers:

5' gatcgaattcgcagcggagtcaggggaa          (SEQ ID NO:4)

5' gatcgcggccgcctattatccaaatcgttccat (SEQ ID NO:5)

in the following 50 µl reaction:
200 ng Cdc14A/pGEX4T-2
375 ng each primer (listed above)
1.5 mM MgSO$_4$
0.4 mM dATP
0.4 mM dCTP
0.4 mM dGTP
0.4 mM dTTP
1× Platinum Taq DNA Polymerase High Fidelity Buffer [60 mM Tris-SO$_4$ pH 8.9, 18 mM (NH$_4$)$_2$SO$_4$] (Gibco-BRL)
2.5 units Platinum Taq DNA Polymerase High Fidelity (Gibco-BRL)

The PCR cycle conditions were as follows:
(94° C. 10 min.) 1×
(94° C. 1 min, 50° C. 1 min, 72° C. 1 min) 12×
(72° C. 5 min) 1×

The resulting PCR product was analyzed on a 1% agarose gel stained with ethidium bromide. The PCR product was purified away from the reactants using a Qiaquick PCR purification column (Qiagen) per manufacturer's instruction.

The PCR product was digested with EcoRI and NotI restriction endonucleases (Gibco-BRL) in a 20 µl reaction containing (~0.5 µg PCR product, 50 mM Tris-HCl pH 8.0, 10 mM MgCl2, 100 mM NaCl, 10 units EcoRI, 10 units NotI) incubated at 37° C. for 2.5 hours.

The expression vector PET30A (Novagen) was digested with EcoRI and NotI restriction endonucleases (Gibco-BRL) in a 20 µl reaction containing (1.5 µg PET30A, 50 mM Tris-HCl pH 8.0, 10 mM MgCl2, 100 mM NaCl, 10 units EcoRI, 10 units NotI) incubated at 37° C. for 2 hours. Following the 2 hour incubation, 1 µl (20 units) of calf intestine alkaline phosphatase (Gibco-BRL) was added and the reaction incubated for another 30 minutes at 37° C.

Following the reactions, the PCR product and PET30A vector were purified from the reactants using a Qiaquick PCR purification column (Qiagen) per manufacturer's instruction.

The PCR product was ligated into the PET30A vector in a 20 µl reaction containing (~10 ng PET30A, 40 ng PCR product, 50 mM Tris-HCl (pH 7.5), 10 mM MgCl$_2$, 10 mM dithiothreitol, 1 mM ATP, 0.5 µg bovine serum albumin, and 2,000 units T4 DNA ligase (New England Biolabs) and incubated at 25° C. for 16 hours.

2 µl of the ligation reaction was used to transform competent E. coli strain TOP10F (Invitrogen) per manufacturer's instruction. E. coli transformants were selected on LB plates containing 50 µg/ml kanamycin. Three kanamycin resistant clones were chosen and grown overnight in a 2.5 ml volume of LB supplemented with kanamycin (50 µg/ml). Plasmid was purified from each clone using an affinity column (Qiagen) per manufacturer's instruction. For verification, plasmids were digested with EcoRI and NotI (as described above) and visualized by agarose gel electrophoresis. One of the recombinant plasmids, designated Cdc14AS plasmid #1, was used to transform competent E. coli strain BL21 DE3 (Novagen), and transformants were selected on LB plates containing 50 µg/ml kanamycin.

Expression and Purification of Cdc14AS Protein:

A single colony of BL21 DE3 transformed with Cdc14AS plasmid #1 was grown overnight at 37° C. in 25 ml LB containing 50 µg/ml kanamycin. The next day, the 25 ml culture was subcultured into 225 ml LB containing 50 µg/ml kanamycin and grown shaking at 37° C. for 1.5 hours until OD$_{600}$=0.5. To induce expression of Cdc14AS, IPTG was added to the culture medium to a final concentration of 0.5 mM and the culture was shaken at 28° C. for 6 hours. Following this induction, the culture was centrifuged at 10,000×g for 10 min at 4° C. The E. coli pellet was resuspended in 30 ml bacterial protein extraction reagent (BPER; Pierce) supplemented with 1M NaCl. The solution was vortex-mixed for 30 seconds and centrifuged at 10,000×g for 10 minutes at 4° C. The supernatant was removed and placed on ice. Imidazole was added to the supernatant to a final concentration of 10 mM, followed by the addition of 3 ml Ni$^{++}$-NTA Superflow (Qiagen). This mixture was shaken gently at 4° C. for 30 minutes, and loaded onto a purification column. The column was washed with 25 ml wash buffer (50 mM imidazole, 0.5 mM NaCl, 20 mM Tris-HCl pH 7.9) and protein was eluted with 3 ml elution buffer (1M imidazole, 0.5 mM NaCl, 20 mM Tris-HCl pH 7.9). The eluate was dialyzed overnight against 3 L of (50 mM Tris-HCl pH 8.0, 300 mM NaCl, 2.5 mM EDTA), and then concentrated using an Amicon YM-10 spin column. Glycerol was added to 10% final concentration, and dithiothreitol was added to 2.5 mM final concentration.

The molecular mass and purity of the protein preparation was determined by SDS-PAGE on a 4–20% gradient gel stained with colloidal blue. To verify the activity of the enzyme, 10 µl of the final cdc14AS protein was incubated with a solution of 100 µg p-Nitrophenyl phosphate (Pierce) in phosphate buffered saline (pH 7.4) for 10 minutes at 37° C. and a yellow color change was observed indicating a positive reaction with phosphatase.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention that are obvious to those skilled in the field of molecular biology or related fields are intended to be within the scope of the following claims.

SEQUENCE LISTING

<160> NUMBER OF SEQ ID NOS: 5

<210> SEQ ID NO 1
<211> LENGTH: 429
<212> TYPE: PRT
<213> ORGANISM: Artificial Sequence
<220> FEATURE:
<223> OTHER INFORMATION: Residues 53-429: Homo sapiens
      Residues 1-52: His-tag and S-tag

<400> SEQUENCE: 1

```
Met His His His His His His Ser Ser Gly Leu Val Pro Arg Gly Ser
 1               5                  10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Ala Asp Ile
```

```
                     35                  40                  45
Gly Ser Glu Phe Ala Ala Glu Ser Gly Glu Leu Ile Gly Ala Cys Glu
     50                  55                  60

Phe Met Lys Asp Arg Leu Tyr Phe Ala Thr Leu Arg Asn Arg Pro Lys
 65                  70                  75                  80

Ser Thr Val Asn Thr His Tyr Phe Ser Ile Asp Glu Glu Leu Val Tyr
                 85                  90                  95

Glu Asn Phe Tyr Ala Asp Phe Gly Pro Leu Asn Leu Ala Met Val Tyr
                100                 105                 110

Arg Tyr Cys Cys Lys Leu Asn Lys Lys Leu Lys Ser Tyr Ser Leu Ser
            115                 120                 125

Arg Lys Lys Ile Val His Tyr Thr Cys Phe Asp Gln Arg Lys Arg Ala
    130                 135                 140

Asn Ala Ala Phe Leu Ile Gly Ala Tyr Ala Val Ile Tyr Leu Lys Lys
145                 150                 155                 160

Thr Pro Glu Glu Ala Tyr Arg Ala Leu Leu Ser Gly Ser Asn Pro Pro
                165                 170                 175

Tyr Leu Pro Phe Arg Asp Ala Ser Phe Gly Asn Cys Thr Tyr Asn Leu
            180                 185                 190

Thr Ile Leu Asp Cys Leu Gln Gly Ile Arg Lys Gly Leu Gln His Gly
        195                 200                 205

Phe Phe Asp Phe Glu Thr Phe Asp Val Asp Glu Tyr Glu His Tyr Glu
210                 215                 220

Arg Val Glu Asn Gly Asp Phe Asn Trp Ile Val Pro Gly Lys Phe Leu
225                 230                 235                 240

Ala Phe Ser Gly Pro His Pro Lys Ser Lys Ile Glu Asn Gly Tyr Pro
                245                 250                 255

Leu His Ala Pro Glu Ala Tyr Phe Pro Tyr Phe Lys Lys His Asn Val
            260                 265                 270

Thr Ala Val Val Arg Leu Asn Lys Lys Ile Tyr Glu Ala Lys Arg Phe
        275                 280                 285

Thr Asp Ala Gly Phe Glu His Tyr Asp Leu Phe Phe Ile Asp Gly Ser
    290                 295                 300

Thr Pro Ser Asp Asn Ile Val Arg Arg Phe Leu Asn Ile Cys Glu Asn
305                 310                 315                 320

Thr Glu Gly Ala Ile Ala Val His Cys Lys Ala Gly Leu Gly Arg Thr
                325                 330                 335

Gly Thr Leu Ile Ala Cys Tyr Val Met Lys His Tyr Arg Phe Thr His
            340                 345                 350

Ala Glu Ile Ile Ala Trp Ile Arg Ile Cys Arg Pro Gly Ser Ile Ile
        355                 360                 365

Gly Pro Gln Gln His Phe Leu Glu Glu Lys Gln Ala Ser Leu Trp Val
    370                 375                 380

Gln Gly Asp Ile Phe Arg Ser Lys Leu Lys Asn Arg Pro Ser Ser Glu
385                 390                 395                 400

Gly Ser Ile Asn Lys Ile Leu Ser Gly Leu Asp Asp Met Ser Ile Gly
                405                 410                 415

Gly Asn Leu Ser Lys Thr Gln Asn Met Glu Arg Phe Gly
            420                 425

<210> SEQ ID NO 2
<211> LENGTH: 377
<212> TYPE: PRT
<213> ORGANISM: Homo sapiens
```

<400> SEQUENCE: 2

```
Ala Ala Glu Ser Gly Glu Leu Ile Gly Ala Cys Glu Phe Met Lys Asp
  1               5                  10                  15
Arg Leu Tyr Phe Ala Thr Leu Arg Asn Arg Pro Lys Ser Thr Val Asn
             20                  25                  30
Thr His Tyr Phe Ser Ile Asp Glu Glu Leu Val Tyr Glu Asn Phe Tyr
         35                  40                  45
Ala Asp Phe Gly Pro Leu Asn Leu Ala Met Val Tyr Arg Tyr Cys Cys
     50                  55                  60
Lys Leu Asn Lys Lys Leu Lys Ser Tyr Ser Leu Ser Arg Lys Lys Ile
 65                  70                  75                  80
Val His Tyr Thr Cys Phe Asp Gln Arg Lys Arg Ala Asn Ala Ala Phe
                 85                  90                  95
Leu Ile Gly Ala Tyr Ala Val Ile Tyr Leu Lys Lys Thr Pro Glu Glu
                100                 105                 110
Ala Tyr Arg Ala Leu Leu Ser Gly Ser Asn Pro Pro Tyr Leu Pro Phe
            115                 120                 125
Arg Asp Ala Ser Phe Gly Asn Cys Thr Tyr Asn Leu Thr Ile Leu Asp
130                 135                 140
Cys Leu Gln Gly Ile Arg Lys Gly Leu Gln His Gly Phe Phe Asp Phe
145                 150                 155                 160
Glu Thr Phe Asp Val Asp Glu Tyr Glu His Tyr Glu Arg Val Glu Asn
                165                 170                 175
Gly Asp Phe Asn Trp Ile Val Pro Gly Lys Phe Leu Ala Phe Ser Gly
            180                 185                 190
Pro His Pro Lys Ser Lys Ile Glu Asn Gly Tyr Pro Leu His Ala Pro
        195                 200                 205
Glu Ala Tyr Phe Pro Tyr Phe Lys Lys His Asn Val Thr Ala Val Val
    210                 215                 220
Arg Leu Asn Lys Lys Ile Tyr Glu Ala Lys Arg Phe Thr Asp Ala Gly
225                 230                 235                 240
Phe Glu His Tyr Asp Leu Phe Phe Ile Asp Gly Ser Thr Pro Ser Asp
                245                 250                 255
Asn Ile Val Arg Arg Phe Leu Asn Ile Cys Glu Asn Thr Glu Gly Ala
            260                 265                 270
Ile Ala Val His Cys Lys Ala Gly Leu Gly Arg Thr Gly Thr Leu Ile
        275                 280                 285
Ala Cys Tyr Val Met Lys His Tyr Arg Phe Thr His Ala Glu Ile Ile
    290                 295                 300
Ala Trp Ile Arg Ile Cys Arg Pro Gly Ser Ile Gly Pro Gln Gln
305                 310                 315                 320
His Phe Leu Glu Glu Lys Gln Ala Ser Leu Trp Val Gln Gly Asp Ile
                325                 330                 335
Phe Arg Ser Lys Leu Lys Asn Arg Pro Ser Ser Glu Gly Ser Ile Asn
            340                 345                 350
Lys Ile Leu Ser Gly Leu Asp Asp Met Ser Ile Gly Gly Asn Leu Ser
        355                 360                 365
Lys Thr Gln Asn Met Glu Arg Phe Gly
    370                 375
```

<210> SEQ ID NO 3
<211> LENGTH: 1131
<212> TYPE: DNA

-continued

```
<213> ORGANISM: Homo sapiens

<400> SEQUENCE: 3
gcagcggagt cagggaact aatcggggct tgtgagttca tgaaagatcg gttatatttt      60
gctactttaa ggaatagacc aaaaagcaca gtaaataccc actatttctc catcgatgag    120
gagctggtct atgaaaattt ctatgcagat tttggaccgc tgaacttggc aatggtgtac    180
agatattgct gcaaactaaa caagaaacta aaatcataca gtttgtcaag aaagaaaata    240
gtgcactaca cctgttttga ccaacggaaa agagcaaatg cagcattttt gataggtgcc    300
tatgcagtaa tctatttaaa gaagacacca gaagaagcct acagagcact cctgtctggc    360
tcaaaccccc cctatcttcc attcagggat gcttcctttg gaaattgcac ttacaatctc    420
accattctcg actgtttgca gggaatcaga aagggattac aacatggatt ttttgacttt    480
gagacatttg atgtggatga atatgaacat tatgagcgag ttgaaaatgg tgacttcaac    540
tggattgttc caggaaaatt tttagcattt agtggaccac atcctaaaag caaaattgag    600
aatggttatc ctcttcacgc ccctgaagcc tactttcctt atttcaaaaa gcataatgtg    660
actgcagttg tgaggctaaa caaaaagatt tatgaggcaa agcgcttcac agacgctggc    720
ttcgagcact atgacctctt cttcatagat ggcagcacac ccagtgacaa catcgtgcga    780
aggttcctga acatctgtga gaacaccgaa ggggccatcg ccgttcactg caaagctggt    840
cttggaagaa cagggacatt gatagcctgt tatgtaatga acactacag gtttacacat    900
gctgaaataa ttgcttggat tagaatatgc cggccaggct ctattatagg accccagcag    960
cacttcctgg aagaaaaaca agcatcgttg tgggtccaag gagacatttt ccgatccaaa   1020
ctgaaaaatc gaccatccag tgaaggaagt attaataaaa ttctttctgg cctagatgat   1080
atgtctattg gtggaaatct ttcaaaaaca caaaacatgg aacgatttgg a            1131

<210> SEQ ID NO 4
<211> LENGTH: 28
<212> TYPE: DNA
<213> ORGANISM: Artificial Sequence
<220> FEATURE:
<223> OTHER INFORMATION: oligonucleotide

<400> SEQUENCE: 4
gatcgaattc gcagcggagt caggggaa                                         28

<210> SEQ ID NO 5
<211> LENGTH: 33
<212> TYPE: DNA
<213> ORGANISM: Artificial Sequence
<220> FEATURE:
<223> OTHER INFORMATION: oligonucleotide

<400> SEQUENCE: 5
gatcgcggcc gcctattatc caaatcgttc cat                                   33
```

That which is claimed is:

. An isolated polypeptide, wherein the amino acid sequence of said polypeptide consists of SEQ ID NO:1.

2. A method for identifying an inhabitor of the polypeptide of claim 1, the method comprising contacting the polypeptide with an agent and determining whether the agent inhibits the phosphatase activity of the polypeptide.

3. A method for identifying an agent that binds to the polypeptide of claim 1, the method comprising coutacting the polypeptide with an agent and determining wheather a complex is formed with the agent bound to the polypeptide.

* * * * *